(12) United States Patent
Soon-Shiong et al.

(10) Patent No.: US 11,585,805 B2
(45) Date of Patent: Feb. 21, 2023

(54) METHODS OF IMMUNOGENIC MODULATION

(71) Applicants: NANT HOLDINGS IP, LLC, Culver City, CA (US); NANTCELL, INC., Culver City, CA (US)

(72) Inventors: Patrick Soon-Shiong, Culver City, CA (US); Kayvan Niazi, Culver City, CA (US); Shahrooz Rabizadeh, Culver City, CA (US)

(73) Assignees: NantCell, Inc., Culver City, CA (US); Nant Holdings IP, LLC, Culver City, CA (US)

( * ) Notice: Subject to any disclaimer, the term of this patent is extended or adjusted under 35 U.S.C. 154(b) by 224 days.

(21) Appl. No.: 16/076,280

(22) PCT Filed: Feb. 16, 2017

(86) PCT No.: PCT/US2017/018214
§ 371 (c)(1),
(2) Date: Aug. 7, 2018

(87) PCT Pub. No.: WO2017/143092
PCT Pub. Date: Aug. 24, 2017

(65) Prior Publication Data
US 2021/0223231 A1    Jul. 22, 2021

Related U.S. Application Data

(60) Provisional application No. 62/297,751, filed on Feb. 19, 2016.

(51) Int. Cl.
*G01N 33/574* (2006.01)
*G01N 33/50* (2006.01)
*G01N 33/68* (2006.01)

(52) U.S. Cl.
CPC ....... *G01N 33/5011* (2013.01); *G01N 33/505* (2013.01); *G01N 33/574* (2013.01); *G01N 33/6878* (2013.01); *G01N 2333/7155* (2013.01)

(58) Field of Classification Search
CPC ............. G01N 33/5011; G01N 33/505; G01N 33/6878; G01N 2333/7155
See application file for complete search history.

(56) References Cited

U.S. PATENT DOCUMENTS

| 7,758,891 B2 | 7/2010 | Desai et al. |
| 7,771,751 B2 | 8/2010 | Desai et al. |

(Continued)

FOREIGN PATENT DOCUMENTS

| CA | 3 014 428 A1 | 8/2017 |
| CN | 1665533 A | 9/2005 |

(Continued)

OTHER PUBLICATIONS

Gong et al. Characterization of a human cell line (NK-92) with phenotypical and functional characteristics of activated natural killer cells. Leukemia 8 (4): 652-528 (1994) Abstract.*

(Continued)

*Primary Examiner* — Gailene Gabel
(74) *Attorney, Agent, or Firm* — Martin Fessenmaier; Umberg Zipser LLP (57) ABSTRACT

Ex vivo determination of increased tumor immunogenicity of a tumor biopsy is used as a guide to identify immunotherapy of a tumor in a patient. Most preferably, the ex vivo tests will include exposure of biopsy samples to stress conditions to produce pretreated tumor cells that are then assayed with immune competent cells for increased activation or activity. Test conditions include exposure of the biopsy samples to immune stimulatory compositions, anti- (Continued)

bodies against neoepitopes, and/or modified cells, and an increase of immunogenicity is preferably determined by their exposure to T cells and/or NK cells.

15 Claims, 1 Drawing Sheet

(56) References Cited

U.S. PATENT DOCUMENTS

| | | | |
|---|---|---|---|
| 7,780,984 | B2 | 8/2010 | Desai et al. |
| 7,981,445 | B2 | 7/2011 | De et al. |
| 8,034,375 | B2 | 10/2011 | Desai et al. |
| 8,034,765 | B2 | 10/2011 | De et al. |
| 8,257,733 | B2 | 9/2012 | Desai et al. |
| 8,268,348 | B2 | 9/2012 | Desai et al. |
| 8,735,394 | B2 | 5/2014 | Desai et al. |
| 8,911,786 | B2 | 12/2014 | Desai et al. |
| 8,927,019 | B2 | 1/2015 | Desai et al. |
| 8,999,396 | B2 | 4/2015 | Desai et al. |
| 9,101,543 | B2 | 8/2015 | Desai et al. |
| 2004/0038339 | A1 | 2/2004 | Kufer et al. |
| 2004/0115708 | A1 | 6/2004 | Ardies |
| 2010/0034772 | A1* | 2/2010 | Dressel ............... A61K 38/1709 424/85.2 |
| 2014/0134128 | A1 | 5/2014 | Wong et al. |
| 2016/0326597 | A1 | 11/2016 | Chan et al. |
| 2018/0141998 | A1* | 5/2018 | Nguyen ............... C12Q 1/6886 |

FOREIGN PATENT DOCUMENTS

| | | |
|---|---|---|
| CN | 103003698 A | 3/2013 |
| CN | 103180730 A | 6/2013 |
| CN | 103421117 A | 12/2013 |
| CN | 104887717 A | 9/2015 |
| CN | 108700566 A | 10/2018 |
| JP | 2011523710 A | 8/2011 |
| JP | 2013541338 A | 11/2013 |
| JP | 2015147770 A | 8/2015 |
| JP | 2019-511903 A | 5/2019 |
| KR | 10-2018-0107257 A | 10/2018 |
| WO | 03/092624 A2 | 11/2003 |
| WO | 2011131246 | 10/2011 |
| WO | 2011/139345 A2 | 11/2011 |
| WO | 2013/062505 A1 | 5/2013 |
| WO | 2014078447 A1 | 5/2014 |
| WO | 2014082729 | 6/2014 |
| WO | 2015154012 | 10/2015 |
| WO | 2016044530 | 3/2016 |
| WO | 2016100975 | 6/2016 |
| WO | 2016128060 | 8/2016 |
| WO | 2016172583 | 10/2016 |
| WO | 2016172722 | 10/2016 |
| WO | 2016207164 | 12/2016 |
| WO | 2017/143092 A1 | 8/2017 |

OTHER PUBLICATIONS

Soriani et al. Chemotherapy-elicited upregulation of NKG2D and DNAM-1 ligands as a therapeutic target in multiple myeloma. Oncolmmunology 2 (12): e26663-1 to e26663-3 (Dec. 2013).*
Intention to grant received for European Patent Application Serial No. 17753857.6 dated Jun. 8, 2020, 46 pages.
Hsin Yi Lu et al., "Synergism through combination of chemotherapy and oxidative stress-induced autophagy in A549 lung cancer cells using redoxresponsive nanohybrids: A new strategy for cancer therapy", Biomaterials, vol. 42 (2015), pp. 30-41.
Qing Li et al., "NK Cell Assays in Immunotoxicity Testing", Methods in Molecular Biology, vol. 598, pp. 207-219 (Cited from Specification). (2010).
Valiathan et al., "Evaluation of a flow cytometry-based assay for natural killer cell activity in clinical settings", Scandinavian Journal of Immunology, 2012, vol. 2012, pp. 455-462 (Cited from Specification).
Extended European Search Report received for European Patent Application Serial No. 17753857.6 dated Aug. 14, 2019, 6 pages.
Corben et al., "Ex Vivo Treatment Response of Primary Tumors and/or Associated Metastases for Preclinical and Clinical Development of Therapeutics", Journal of Visualized Experiments, Oct. 2014, vol. 92, No. e52157, pp. 1-7.
Silva et al., "An Organotypic High Throughput System for Characterization of Drug Sensitivity of Primary Multiple Myeloma Cells", Journal of Visualized Experiments, 2015, vol. 101, No. e53070, pp. 1-12.
Hillerdal et al., "Ex vivo evaluation of tumor cell specific drug responses in malignant pleural effusions", Oncotarget, 2017, vol. 8, No. 47, pp. 82885-82896.
Silva et al., "An Ex Vivo Platform for the Prediction ofClinical Response in Multiple Myeloma", Cancer Research, Jun. 15, 2017, vol. 77, No. 12, pp. 3336-3351.
Pauli et al., "Personalized In Vitro and In Vivo CancerModels to Guide Precision Medicine", Cancer Discovery, May 2017, pp. OF1-OF16.
Communication pursuant to Article 94(3) EPC received for European Patent Application Serial No. 17753857.6 dated Feb. 21, 2020, 7 pages.
Notice of Reasons for Refusal received for Japanese Patent Application Serial No. 2018-538100 dated Nov. 19, 2019, 8 pages (Including English Translation).
Notification of Reason for Refusal received for Korean Patent Application Serial No. 10-2018-7026268 dated Feb. 25, 2020, 5 pages (Including English Translation).
International Search Report received for PCT Application Serial No. PCT/US2017/018214 dated May 30, 2017, 13 pages.
International Preliminary Report on Patentability Chapter I received for PCT Application Serial No. PCT/2017/018214 dated Aug. 30, 2018, 11 pages.
Spear et al., "NKG2D ligands as therapeutic targets", Cancer Immunity, May 1, 2013, vol. 13, No. 8, pp. 1-14.
Soriani et al., "Chemotherapy-elicited upregulation of NKG2D and DNAM-1 ligands as a therapeutic target in multiple myeloma", Oncoimmunology, Dec. 2013, vol. 2, No. 12, pp. 1-3.
Son et al., "Synergistic enhancement of NK cell-mediated cytotoxicity by combination of histone deacetylase inhibitor and ionizing radiation", Radiation Oncology, 2014, vol. 9, No. 49, pp. 1-10.
Table Reflecting the Drugs and their effects on tumour and immune system along with the current and experimental mmunotherapy combinations. (2012).
First Office Action received for Chinese Patent Application Serial No. 201780007358 9 dated Jan. 29, 2021, 31 pages (Including English Translation).
Stoklasek et al., "Combined IL-15/IL-15Rα Immunotherapy Maximizes IL-15 Activity In Vivo", The Journal of Immunology, 2006, vol. 177, pp. 6072-6080.
Decision of Refusal received for Japanese Patent Application Serial No. 2018538100 dated Aug. 18, 2020, 8 pages (Including English Translation).
Mahoney et al., "Combination cancer immunotherapy and new immunomodulatory targets" Nature Reviews, Drug Discovery, vol. 14, Aug. 2015.
Kahraman et al., "Major Histocompatibility Complex Class I-Related Chains A and B (MIC A/B): A Novel Role in Nonalcoholic Steatohepatitis" Hepatology, vol. 51, No. 1, 2010.
Campoli et al., "HLA antigen and NK cell activating ligand expression in malignant cells: a story of loss or acquisition" Semin Immunopathol, vol. 33, pp. 321-334, 2011.
Notification of Reason for Refusal received for Korean Patent Application Serial No. 10-2018-7026268 dated Oct. 28, 2020, 5 pages (Including English Translation).
Notice of Final Rejection received for Korean Patent Application Serial No. KR20187026268 dated Jan. 5, 2021 2 Pages (Including English Translation).
Office Action received for Israel Patent Application Serial No. 261089 dated Aug. 15, 2021, 6 pages.( Including English Translation).

(56) References Cited

OTHER PUBLICATIONS

Second Office Action received for Chinese Patent Application Serial No. 201780007358.9 dated Aug. 23, 2021, 7 pages.(Including English Translation).
Third Office Action received for Chinese Patent Application Serial No. 201780007358.9 dated Feb. 15, 2022, 10 pages. (Including English Translation).

* cited by examiner

METHODS OF IMMUNOGENIC MODULATION

This application claims priority to U.S. provisional application Ser. No. 62/297,751, filed Feb. 19, 2016.

FIELD OF THE INVENTION

The field of the invention is compositions and methods for ex vivo treatment of a cancer to identify patient treatment options that increase immunogenicity of the cancer in vivo.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Personalized medicine based on genomic or proteomic insights from a diseased tissue has become an increasingly promising tool in cancer therapy. However, and despite the significant amount of information that can be obtained from relatively small quantities of diseased tissue, treatment is typically limited to a comparatively low number of experimental or approved drugs with well-characterized targets. For example, treatment of breast cancer with antibodies that target mutant form of HER2 (trastuzumab) can improve outcome where the tumor overexpresses the HER2 protein. Likewise, where cancer growth is driven by a pathway that includes a kinase, treatment may be effective with kinase inhibitors targeting such kinases (e.g., inhibition of EGFR using afatinib, erlotinib, etc., or inhibition of Bcr-Abl with bosutinib, imatinib, etc.). However, cancers will in many cases develop resistance against specific drugs and growth often resumes.

Alternatively or additionally, cancer treatment may also include immunotherapy to help eradicate aberrant cells using one or more components of the immune system. For example, immunotherapy may involve cytokines and/or immune checkpoint inhibitors to stimulate an immune response, while in other examples cells or modified cells are employed as therapeutic agents. In yet other examples, cancer vaccines have been reported to be at least partially effective in certain diseases. Unfortunately, immune based cancer therapies are often highly unpredictable as the efficacy depends in most cases on the specific epitopes presented and/or available to the patient's immune system, and the health of the patient's immune system (which is often already compromised by prior chemotherapeutic treatments). Moreover, many tumors also exhibit strong immune evasion, and immunotherapy must account for such mechanisms, which are generally not well understood.

Some tried to solve the problem by identifying patient-specific neoepitopes and using them in the immunotherapy. For example, WO 2016/172722 discloses cancer neoepitopes and methods of using neoepitopes to generate synthetic antibodies for immunotherapy. In another example, US 2016/0326597 discloses use of neoepitopes in a patient's cancer sample where some neoepitopes have stronger binding affinities to certain MHC complexes than others. By identifying neoepitopes with stronger binding affinities, those neoepitopes can be used to identify individuals who are likely to respond to a treatment by administering immune checkpoint modulator. Others attempted to develop patient-specific tumor treatments that target individual expression patterns of tumor antigens (see e.g., WO 2014/082729) for stimulating, priming and/or expanding T cells directed against cells expressing antigens.

Still others tried to solve the problem of inconsistent immune response by determining the susceptibility of an individual patient to a cancer treatment, especially to immunotherapy. For example, WO 2011/131246 discloses ex vivo methods for determining the susceptibility of a tumor to a cancer treatment by evaluating expression of stress response markers or macroautophagic response markers.

However, none of those contemplate expression of neoepitopes and other markers on cancer cells may vary depending on stress conditions given to the cancer cells, and as such fail to recognize their variability among patients. Therefore, even though there are many treatment options for cancer known in the art, all or almost all of them suffer from several disadvantages. Consequently, there remains a need for improved systems and methods of cancer therapy.

SUMMARY OF THE INVENTION

The inventive subject matter is directed to various systems, compositions, and methods to increase immunogenicity of a tumor via specific treatment(s) and to use such treatment(s) alone or in combination with immune stimulation to eradicate the tumor and to form immune memory against the tumor.

In one aspect of the inventive subject matter, the inventors contemplate a method of identifying a treatment option for a patient that includes a step of exposing ex vivo a plurality of tumor biopsy samples of the patient to a respective and distinct plurality of stress conditions to produce respective pretreated tumor cells. In another step, the pretreated tumor cells are then contacted with a plurality of immune competent cells, and a response of the immune competent cells to the pretreated tumor cells is quantified. In still another step, a stress condition is selected as a treatment option when the response meets or exceeds a predetermined threshold.

Among other possibilities, suitable stress conditions include low-dose chemotherapy (e.g., metronomic low-dose), exposure to low-dose irradiation, heat shock treatment, hypoxia, hyperoxia, exposure to chronic inflammation condition, exposure to reactive oxygen species, exposure to a native or modified immune T- or NK cell, exposure to an antibody, and/or environmental stress condition (e.g., DNA damaging agent, a HSP90 inhibitor, a GSK3 inhibitor, viral infection).

Stress conditions may result in a variety of markers expressed on the stressed cell, including over-expression of NKG2D ligand (relative to the same cell without exposure to the stress condition), expression of checkpoint inhibitor ligands, expression of neoepitopes, or may result in the activation or deactivation of signaling pathways (e.g., apoptosis pathway, cell division pathway) etc.

In addition, it is contemplated that the plurality of biopsy samples may be exposed to an immune stimulant, and especially contemplated immune stimulants include cytokines (e.g., IL-15, IL-15 superagonist, IL-2, IL-7, IL-21), TLR ligands (e.g., PAMPs DAMPs), and/or checkpoint inhibitors.

Where desired, it is also contemplated that suitable methods may include a step of determining one or more neoepitopes on the biopsy samples, against which an antibody or other binding molecule may be generated. Additionally, a viral vector or recombinant virus may be generated that contains a recombinant nucleic acid encoding one or more neoepitopes, and it is especially preferred that the immune competent cells will be transformed with the viral vector or recombinant virus. Moreover, one or more further neoepitopes may be determined for the pretreated tumor cells after the pretreated tumor cells were contacted with the immune competent cells. Most typically, the immune competent cells are T cells and/or NK cells (and especially NK92 cells or genetically engineered NK cells such as aNK cells, haNK cells, or taNK cells).

With respect to the step of quantifying the response of the immune competent cells, one or more of a microscopic assay, a luminescent assay, a fluorescent assay, and a radiological assay are especially contemplated. Thus, the predetermined threshold may be a predetermined rate of lysis or apoptosis of the pretreated tumor cells, but may also be a colorimetric or fluorimetric signal.

Various objects, features, aspects and advantages of the inventive subject matter will become more apparent from the following detailed description of preferred embodiments, along with the accompanying drawing FIGUREs in which like numerals represent like components.

DETAILED DESCRIPTION

The inventive subject matter provides systems and methods of identifying treatment options for a patient, especially by identification of conditions that increase immunogenicity of a tumor via specific treatment(s) and to use such treatment (s) alone or in combination with immune stimulation.

While the inventive subject matter is susceptible of various modification and alternative embodiments, certain illustrated embodiments thereof are shown in the drawings and will be described below in detail. It should be understood, however, that there is no intention to limit the invention to the specific form disclosed, but on the contrary, the invention is to cover all modifications, alternative embodiments, and equivalents falling within the scope of the claims. The following discussion provides many examples of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Figure 1:
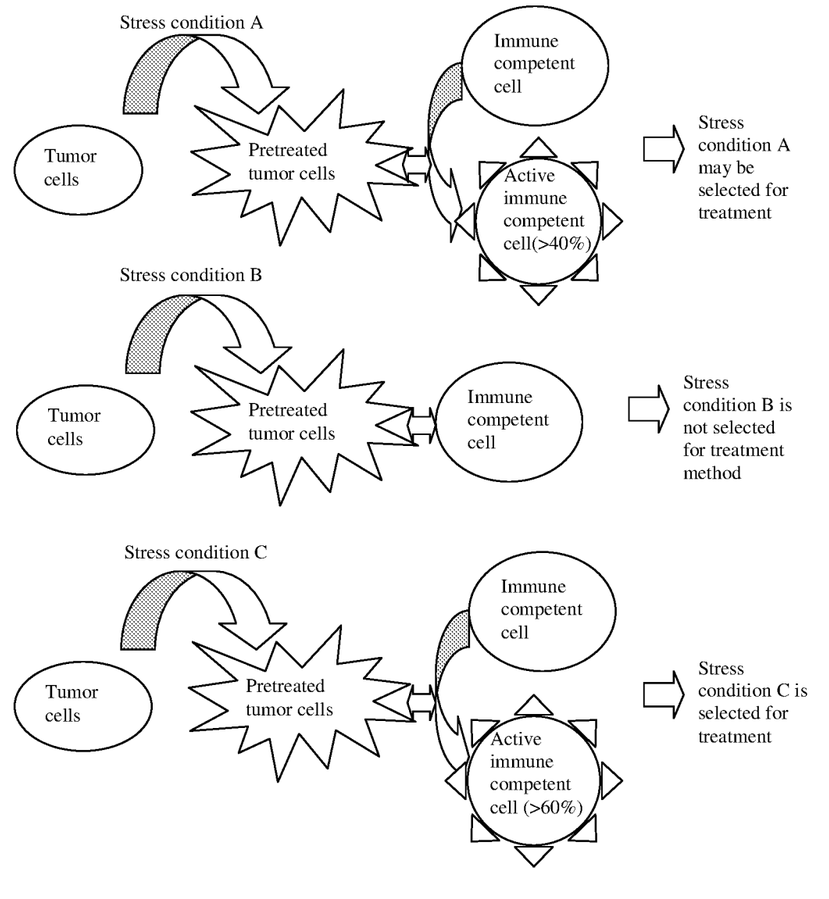
FIG. 1 illustrates an exemplary method of identifying treatment for a patient by interrogating immunogenicities of cancer cells using various stress conditions.

The inventor has now discovered that a tumor in a patient may be more effectively treated by rendering the tumor more immunogenic using an intervention that was previously identified in a series of ex vivo treatments using tumor biopsies. As used herein, the term "immunogenic" means a characteristic of a cell that produces or facilitates an immune response, or that leads to activation of immune cells contacting the "immunogenic" cells in vitro, ex vivo, or in vivo. Thus, in one aspect of the inventive subject matter, the inventor contemplates a method of identifying treatment options for a patient by inducing a tumor or cancer cells to become more immunogenic. FIG. 1 shows one exemplary illustration of contemplated methods. Here, one step includes exposing ex vivo a plurality of biopsy samples from a tumor of the patient to a respective and distinct plurality of stress conditions.

In a preferred embodiment, live tissue from a patient's tumor biopsy is split into a plurality of samples so that each sample can be exposed to different types/conditions of stress conditions. For example, a tumor biopsy is taken from a patient diagnosed with small cell lung cancer, and the biopsy is split into a plurality of samples (e.g., at least 2, at least 4, at least 10, at least 20, or at least 50, etc.). Of course, it should be appreciated that the biopsy need not be limited to solid tumors, but that circulating tumor cells as well as blood borne cancers (e.g., various lymphomas such as CML, AML, ALL, etc.) are also expressly deemed suitable for use herein.

As used herein, distinct stress conditions are stress conditions that can be induced in the tumor cells independently and separately (e.g., by treatment performed at different time points, by treatments using different chemicals, etc.). For example, in some embodiments, a stress condition can be induced by a single cause of stress (e.g., heat only, a single chemical only, etc.). In other embodiments, a stress condition can be induced by multiple causes of stress. For example, a stress condition can be induced by treatment of one stress cause A and another stress cause B at the same time. For another example, a stress condition can be induced by treatment of one stress cause A and another stress cause B sequentially. It is also contemplated that multiple treatments of one stress cause A (e.g., heat shock for 1 min for 3 times with a time interval 1 min in between) and a single treatment of one stress cause A (e.g., a single heat shock for 1 min or 3 min) are two different distinct stress conditions.

In further contemplated examples, stress conditions can include metronomic low-dose chemotherapy. Most typically, low dose treatments will be at exposures that are equal or less than 70%, equal or less than 50%, equal or less than 40%, equal or less than 30%, equal or less than 20%, equal or less than 10%, or equal or less than 5% of the $LD_{50}$ or $IC_{50}$ for the chemotherapeutic agent. Additionally, where advantageous, such low-dose regimen may be performed in a metronomic manner as described, for example, in U.S. Pat. Nos. 7,758,891, 7,771,751, 7,780,984, 7,981,445, and 8,034,375. With respect to the particular drug used in such low-dose regimen, it is contemplated that all chemotherapeutic agents are deemed suitable. Among other suitable drugs, kinase inhibitors, receptor agonists and antagonists, anti-metabolic, cytostatic and cytotoxic drugs are all contemplated herein. However, particularly preferred agents include those identified to interfere or inhibit a component of a pathway that drives growth or development of the tumor. Such drugs can be identified using pathway analysis on omics data as described in, for example, WO 2011/139345 and WO 2013/062505.

In some embodiments, contemplated stress conditions may also include one or more environmental stress condition. For example, a portion of cancer cells from biopsy samples can be exposed to radiation, preferably low-dose radiation. In this example, cancer cells can be subjected to various dosages of radiation and typical dosages will be in the range of 0.01-0.1 Gy, 0.1-1 Gy, 1-10 Gy, 10-100 Gy, and in some cases even higher. The radiation may come from various sources and may employ gamma radiation, alpha particle exposure, and/or beta emitters. However, gamma radiation or X-ray exposure is typically preferred. Most typically, and where radiation is employed as stress condition, additional chemotherapeutic agents will include drugs that interfere with double strand DNA repair and homologous strand exchange repair.

For another example, environmental stress condition may include exposure of cancer cells to heat (e.g., typically at least 40° C., at least 42° C., at least 45° C., or at least 47° C.) for various time ranges (e.g., 10 seconds, 1 min, 5 min, 10 min, etc.) and, where desired, with various intermissions between each exposure to the environmental stress condition (e.g., single exposure, multiple exposures with 1 min intervals, multiple exposures with various time intervals, etc.).

For still another example, environmental stress condition may include deprivation of oxygen to mimic tumor hypoxia. Here, at least a portion of cancer cells can be maintained in hypoxia (e.g., less than 15%, less than 10%, less than 5%, less than 3%, less than 1% $O_2$) for a predetermined time (e.g., at least 1 hour, at least 24 hours, at least 3 days, at least 1 week, at least 3 weeks, etc.). Likewise it is contemplated that hyperoxic conditions may be included. For example, at least a portion of cancer cells can be maintained in hyperoxic conditions (e.g., more than 22%, more than 25%, more than 30%, more than 35% $O_2$) for a given time (e.g., at least 1 hour, at least 24 hours, at least 3 days, at least 1 week, at least 3 weeks, etc.).

In some embodiments, environmental stress condition may include mimicking chronic inflammation by administering physiological amounts of inflammation-related reagents. In these embodiments, inflammation-related reagents may include cytokines involved in tumor development including tumor necrosis factor (TNF-$\alpha$), Interleukin 6 (IL-6), Interleukin 10 (IL-10), Transforming Growth Factor (TGF-$\beta$). Additionally or alternatively, environmental stress condition may also include exposure of cancer cells to chronic oxidative stress and/or exposure to radicals. For example, the biopsy samples can be exposed to exogenous hydrogen peroxide ($H_2O_2$) as a source of reactive oxygen species (ROS) at low doses (e.g., between 10 µM-20 µM, 20 µM to 30 µM, 30 µM to 40 µM, etc.) for an acute period (e.g., 12 hours, 24 hours, 48 hours, 7 days, etc.) or high doses (e.g., between 100 µM-200 µM, 200 µM to 300 µM, 300 µM to 400 µM, etc.) for a chronic period (e.g., 1 month, 3 months, 6 months, etc.).

In still another example, environmental stress conditions may include exposure of the cancer cells to one or more chemicals or conditions including various DNA damaging agents (e.g., DNA intercalating agents, methylating agents, strand breaking agents, UV irradiation to induce dimmers, etc.), peptides or reagents that can induce endoplasmic reticulum (ER) stress induced apoptosis of cells (e.g., heat shock protein (HSP)90 inhibitors, glycogen synthase kinase3 (GSK3) inhibitors, protein N-glycosylation inhibitor (e.g., tunicamycin, etc.), protein transport blocker (e.g., brefeldin A, etc.), calcium uptake inhibitor to ER (e.g., thapsigargin, etc.)).

In some embodiments, environmental stress condition may include exposure of cancer cells to one or more types of viruses that are related to various types of cancer. For example, such viruses includes human papilloma virus (HPV), Epstein-Barr virus (EBV), Hepatitis B virus (HBV), and/or hepatitis C virus (HCV), Human immunodeficiency virus (HIV), Human herpes virus 8 (HHV-8), Human T-lymphotrophic virus-1 (HTLV-1), Merkel cell polyomavirus (MCV), and/or Simian virus 40 (SV40). As will be readily appreciated, the infection dose and exposure time may vary depending on the dormancy and activity of virus, types of cancer cells, and other individual patient's conditions.

It is contemplated that conditions (e.g., duration, frequency, time, dose, concentration, etc) of stress conditions discussed above are effective to directly or indirectly induce tumor cells to produce pretreated tumor cells. As used herein, pretreated tumor cells are tumor cells that express at least one distinct feature than the tumor cell before treatment with stress conditions. For example, in some embodiments, the stress condition is effective to affect protein expression, cell cycle, and/or susceptibility to apoptosis. For example, pretreated tumor cells may change expression level of one or more cellular proteins (e.g., cell surface receptor protein, nuclear receptor protein, secreted protein, including proteins associated with damage-associated molecular patterns (DAMPS), interferons, and cytokines, etc.) and/or nucleotides (e.g., mRNA, microRNA, etc.). For another example, pretreated tumor cells may change their morphology or interaction with environment (e.g., cell shape, level of adherence with other cells or extracellular matrix, etc). For another example, pretreated tumor cells my change activity of cellular proteins and especially proteins associated with signaling and cell cycle (e.g., kinases, phosphatases, heat shock proteins, glycosylases, etc.).

While not wishing to be bound by any particular theory or hypothesis, the inventor also contemplates that at least a portion of the pretreated tumor cells from biopsy sample (e.g., at least 20%, preferably at least 40%, more preferably at least 60%) exposed to the stress conditions will expose or present one or more antigenic epitopes or other signals in amount sufficient to trigger NK-cell and/or T-cell (CD4+ and/or CD8+) activation. In one preferred embodiment, at least a portion of the pretreated cancer cells from the biopsy sample (e.g., at least 20%, preferably at least 40%, more preferably at least 60%) shows higher expression level (e.g., at least 20% higher, at least 30% higher, at least 50% higher, etc.) or higher cell surface expression level of stress markers, and especially NKG2D ligands (e.g., MICA, MICB, RAET1E/ULBP4, RAET1G/ULBP5, RAET1H/ULBP2, RAET1/ULBP1, RAET1L/ULBP6, RAET1N/ULBP3, etc.) relative to tumor cells from the same biopsy sample without exposure to the same stress condition. Likewise, at least a portion of the pretreated cancer cells from the biopsy sample may also express and/or present on their surface one or more neoepitopes in response to the stress conditions.

Regardless of the particular type of stress condition, it is generally contemplated that the stress conditions and conditions of providing stress conditions to the cancer cells are selected such as to avoid immediate cell death. In a preferred embodiment, an optimal or desired condition of providing stress conditions can be determined based on a predetermined threshold. For example, the predetermined threshold may be a predetermined rate of lysis or apoptosis of the pretreated tumor cells. Therefore, conditions are typically adjusted to have a cell killing effect on less than 50%, and more typically less than 30%, even more typically less than 10%, and most typically less than 5% of all cells in the tissue. Therefore, the so pretreated tumor cells will be viable after treatment (but may have a reduced proliferation rate) and most preferably exhibit a substantially altered gene expression profile (which may be established in a subsequent omics analysis, and especially via transcriptomics and/or proteomics analysis). Depending on the particular type of stress condition and severity, the pretreatment may be performed over a few seconds to several days. Where appropriate, pretreated cells may be allowed to recover for several hours to several days prior to being contacted with immune competent cells.

In an especially preferred embodiment, the pretreated cancer cells are then exposed to or contacted with immune competent cells. As used herein, the term 'immune competent cell' includes any cell that is involved in the generation, propagation, or maintenance on an immune response, and therefor especially includes cells contributing to innate and/or adaptive immunity. Thus, especially contemplated immune competent cells include antigen presenting cells, and especially dendritic cells, T cells, NK cells, etc. In particularly preferred aspects, immune competent cells include NK92 cells, allogenic NK92 cells that are modified to be constitutively active or have specificity towards a neoepitope, or genetically engineered NK cells (e.g., aNK cells, haNK cells, or taNK cells). Alternatively, immune competent cells also include CD4+ and/or CD8+ T cells that may be naive to the patient or allogeneic (optionally modified to be constitutively active or have specificity towards a neoepitope such as via a chimeric T-cell/antigen receptor). In further embodiments, the immune competent cells may also be mixtures of cells, and especially immune competent cells from the patient from which the biopsy was obtained. For example, such mixtures may be unpurified (e.g., whole blood), partially purified (e.g., buffy coat), or isolated cell types (e.g., dendritic cells or macrophages or T cells).

Typically, when the immune competent cell used is an NK cell, the ratio of the treated tumor cells to NK cells is between 10,000:1 to 1:10,000, more typically between 1,000:1 to 1:1,000, and most typically between 10:1 to 1:10. There are numerous NK cells suitable for use herein, and especially contemplated NK cells include aNK cells, haNK cells, and taNK cells as described by NantKwest, Inc. (9920 Jefferson Blvd., Culver City, Calif. 90232; see http://nantkwest.com/platform/). Where the cells are genetically modified to have affinity against an epitope, it is especially preferred that such epitopes are neoepitopes that are likely to elicit strong immune responses (i.e., HLA-matched patient and tumor specific neoepitope).

In further contemplated aspects, it should be noted that at least some cancer cells from the biopsy samples that have been subjected to the stress conditions can effectively activate or increase the response of the immune competent cells. In some embodiments, the response of immune competent cells and/or stressed cells can be assessed by immunotoxicity testing. For example, where the immune competent cells are NK cells, killing effect of the NK cells may be assessed using a microscopic assay (e.g., to detect deformation of loss of shape), a luminescent assay (e.g., to detect leaking of a luminogenic agent), a fluorescent assay (e.g., to detect transport or delivery of a lytic agent), or a radiological assay (e.g., to detect leaking of an isotope). Viewed from a different perspective, the killing effect by NK or other immune competent cells may be a measure of immunogenicity of the so pretreated tumor cells. In the same manner, anticipated increased immunogenicity may also be evidenced by a change in a physical parameter of the tumor cell (e.g., increase or decrease in size, density, change in shape or adhesion to substrate). Any suitable methods of detecting the killing effect of immune competent cell are contemplated. For example, immunogenicity of the so treated cells may be determined by determining cytolytic activity against target tumor cells by (51)Cr-release assay, or by determining intracellular levels of perforin, granzymes, and granulysin using flow cytometry (see e.g., Methods Mol Biol. 2010; 598:207-19; Scand J Immunol. 2012 April; 75(4):455-62; or xCELLigence System by Acea Biosciences Inc.).

In other embodiments, the response of immune competent cells includes relative expression levels of cell surface receptor proteins. For example, NK cell activation is determined by the balance of inhibitory (e.g., Killer-cell immunoglobulin-like receptors (KIRs), LIR (leukocyte inhibitory receptors), inhibitory isoform of Ly49) and activating receptor (NCR (natural cytotoxicity receptors), CD94: NKG2 heterodimers, CD16 (FcγIIIA), activating isoform of Ly49, etc.) stimulation. Thus, in these embodiments, the differential and relative expression of proteins can be quantified by any suitable methods to detect protein expressions and/or localizations, such as by FACS assay, a microscopic assay, a luminescent assay, a fluorescent assay, a radiological assay, a western blot, etc.

It is contemplated that stronger response (e.g., higher cytokine and/or chemokine release, higher expression level of some cell surface receptor proteins, stronger cytolytic activity, etc.) of immune competent cells is likely to reflect higher immunogenicity of the pretreated cancer cells. In some embodiments, the quantification of immune competent cell responses can be statistically evaluated to determine which stress condition(s) are more effective to induce the response compared to other stress conditions. When more effective stress condition(s) is used to elicit immune cell response, it is likely that such immune competent cells can more efficiently and effectively elicit immune response against cancer cells in vivo when the patient is treated with the immune competent cells. Thus, it should be appreciated that the immune cell (e.g., NK cell, etc.) response in those assays may be used as a predictive indicator of likely treatment success.

It is also contemplated that not all stress conditions provided to the cancer cells are likely elicit same immune responses to the immune competent cells contacting the cancer cells. In other words, immunogenicity of the cancer cells may vary depending on the stress conditions. Effectiveness of some stress conditions may vary depending on the type of cancer. For example, stress condition A can be effective to induce immunogenicity of cancer cells of non-small cell lung cancer, but may not be effective to induce immunogenicity of cancer cells of large cell neuroendocrine tumors. Effectiveness of some stress conditions may vary among patients suffering even the same type of cancer. For other example, stress condition A can be effective to induce immunogenicity of cancer cells of breast cancer of patient X, stress condition B may not be effective to induce immunogenicity of cancer cells of breast cancer of patient Y. Thus, it should be appreciated that this method can be used to identify effective treatment method provide a platform for personalized immunotherapy that will maximize the response of a patient's specific immune system against the patient specific tumor.

While providing a stress condition may be effective to elicit immunogenicity of cancer cells exposed to the stress condition, it is contemplated that co-treatment or co-administration of immune stimulants along with stress conditions can further enhance immunogenicity of cancer cells. Any suitable types of immune stimulants that can increase or modulate immunogenicity of cancer cells are contemplated. For example, immune stimulants may include stimulatory cytokines (e.g., interleukin (IL)-15, IL-15 superagonist, IL-2, IL-7, IL-21, etc.), and one or more Toll-like receptor (TLR) ligands (e.g., fibrinogen, heparan sulfate fragments, hyaluronic acid fragments, HSP70, etc.). In some embodiments, immune stimulants may also include one or more checkpoint inhibitor(s) that facilitate an immune system attack on cancer cells (e.g., ipilimumab (Yervoy®), pembrolizumab (Keytruda®), and nivolumab (Opdivo®)).

In some embodiments, two or more different immune stimulants can be provided with the stress condition. In these embodiments, the ratio among two or more different immune stimulants can vary depending on the type and stage of cancer and characteristics of the patient (e.g., age, gender, health status, etc.), the type of stress conditions, and the timing of co-treatments of the immune stimulants. For example, immune stimulants can be treated concurrently with the stress condition, after treatment of the stress condition (e.g., a minute after, an hour after, a day after completion of the stress condition, etc.). In still further embodiments, immune stimulants can be administered before subjecting the biopsy to the stress condition (e.g., a minute before, an hour before, a day before initiation of the stress condition, etc.).

It is contemplated that immunogenicity of cancer cells may be strongly intertwined with the expression of at least some neoepitopes in the cancer cell. Thus, neoepitopes may be used to generate antibodies that are then used to target the treated biopsy cells, and/or which may be used to generate a viral vector that contains a recombinant nucleic acid that encodes at least one of the plurality of neoepitopes (the biopsy samples or pretreated cells may then be exposed to the viral vector).

Thus, ex vivo treatment of tumor biopsies to identify the most effective therapy may also be augmented with identification of neoepitopes present in the tumor cells. Neoepitopes can be characterized as expressed random mutations in tumor cells that created unique and tumor specific antigens. Therefore, viewed from a different perspective, neoepitopes may be identified by considering the type (e.g., deletion, insertion, transversion, transition, translocation) and impact of the mutation (e.g., non-sense, missense, frame shift, etc.), which may as such serve as a first content filter through which silent and other non-relevant (e.g., non-expressed) mutations are eliminated. It should further be appreciated that neoepitope sequences can be defined as sequence stretches with relatively short length (e.g., 7-11 mers) wherein such stretches will include the change(s) in the amino acid sequences. Most typically, the changed amino acid will be at or near the central amino acid position. For example, a typical neoepitope may have the structure of $A_4$-N-$A_4$, or $A_3$-N-$A_5$, or $A_2$-N-$A_7$, or $A_5$-N-$A_3$, or $A_7$-N-$A_2$, where A is a proteinogenic amino acid and N is a changed amino acid (relative to wild type or relative to matched normal). For example, neoepitope sequences as contemplated herein include sequence stretches with relatively short length (e.g., 5-30 mers, more typically 7-11 mers, or 12-25 mers) wherein such stretches include the change(s) in the amino acid sequences.

Thus, it should be appreciated that a single amino acid change may be presented in numerous neoepitope sequences that include the changed amino acid, depending on the position of the changed amino acid. Advantageously, such sequence variability allows for multiple choices of neoepitopes and so increases the number of potentially useful targets that can then be selected on the basis of one or more desirable traits (e.g., highest affinity to a patient HLA-type, highest structural stability, etc.). Most typically, neoepitopes will be calculated to have a length of between 2-50 amino acids, more typically between 5-30 amino acids, and most typically between 9-15 amino acids, with a changed amino acid preferably centrally located or otherwise situated in a manner that improves its binding to major histocompatibility complex (MHC). For example, where the epitope is to be presented by the MHC-I complex, a typical neoepitope length will be about 8-11 amino acids, while the typical neoepitope length for presentation via MHC-II complex will have a length of about 13-17 amino acids. As will be readily appreciated, since the position of the changed amino acid in the neoepitope may be other than central, the actual peptide sequence and with that actual topology of the neoepitope may vary considerably.

Preferably, the neoepitopes show de novo expression or enhanced expression when the cancer cells are exposed to one or more stress conditions. Thus, identification of neoepitopes that expresses or shows enhanced expression can be identified by various omics analysis including nucleic acid sequencing, and particularly NGS methods operating on DNA (e.g., Illumina sequencing, ion torrent sequencing, pyrosequencing, nanopore sequencing, etc.), RNA sequencing (e.g., RNAseq, reverse transcription based sequencing, etc.), and protein sequencing or mass spectroscopy based sequencing (e.g., SRM, MRM, CRM, etc.). Further detailed methods of DNA sequencing, RNA sequencing, protein sequencing, and computational analysis of those sequencing results are described in detail in an international patent application No. PCT/US16/65412, which is incorporated herein in its entirety.

It is contemplated that many cancer cells showing enhanced immunogenicities after exposure to the effective stress condition may exhibit different expression of neoepitopes. For example, cancer cells may express different types of neoepitopes after exposure to the effective stress condition. For other example, cancer cells may express a plurality of neoepitopes in different ratio. For still another example, cancer cells may express a plurality of neoepitopes and such plurality of neoepitopes may show different half-life or cell surface stability (e.g., due to trafficking to the cell surface, endocytosis, etc.). Thus, it is still further contemplated that suitable methods will include a further step of determining types and/or expressions of neoepitopes for the biopsy samples before exposure to the stress condition and/or immune stimulants, and determining types and/or expressions of neoepitopes for the pretreated tumor cells after the step of contacting the pretreated tumor cells with a plurality of immune competent cells.

Further, it is also contemplated that some neoepitopes are common between cancer cells and non-cancer cell of a patient. In this scenario, treatment methods targeting those epitopes can induce autoimmune symptoms, which would be undesirable. Thus, the method preferably includes a step of determining types/expressions of neoepitopes for the biopsy samples in the cancer cells, and determining types/expressions of neoepitopes for non-cancer cells of the same patient (or even from same biopsy samples), and comparing the epitope expressions of those. For example, a portion of the tumor biopsy and a matched normal sample of the patient (non-tumor sample of the same patient, e.g., peripheral blood mononuclear cell (PBMC) sample) are also subjected to omics analysis. In especially preferred aspects, the omics analysis includes whole genome sequencing, exome sequencing, RNA sequencing (preferably quantitative with transcription level determination), and/or proteomics analysis (predictive from nucleic acid, and more preferably analytic from tissue sections or formalin-fixed paraffin-embedded (FFPE) samples).

So obtained omics analysis is then used to identify tumor neoepitopes, which are further analyzed for transcription level (i.e., whether or not transcribed and to what extent) and HLA-match with the patients HLA-type. Suitable methods for identification and use of neoepitopes are disclosed in our co-pending U.S. application Ser. No. 15/292,021, filed Oct. 12, 2016, Ser. No. 15/292,021, filed Oct. 12, 2016, and HLA-prediction based on omics data is described in our co-pending international patent application PCT/US16/48768, filed Aug. 25, 2016. Neoepitopes can then be used in a cancer vaccine for treatment as described in co-pending international patent application PCT/US16/65412, filed Dec. 7, 2016. All those references are incorporated herein in their entireties.

Once one or more neoepitopes are identified that are likely to contribute or even cause immunogenicity of the cancer cell, it is also contemplated that those neoepitopes can be overexpressed in the cancer cell to further augment the immunogenicity of the cancer cell. For example, neoepitope A is specifically and highly upregulated/expressed in the cancer cell upon providing one or more stress conditions. In this scenario, the whole or a fragment of neoepitope A can be cloned into a viral vector or a vector for mammalian transfection (e.g., with a marker such as fluorescene, or antibiotics resistance), and delivered into an immune competent cell, and especially a dendritic cell, to so help generate an immune response. In addition, or alternatively, pathway analysis can be performed to identify one or more alternate, non-stress conditions that will lead to overexpression of neoepitope A. Among other suitable pathway analysis tools, PARADIGM is particularly preferred (see e.g., WO 2011/139345 or WO 2013/062505).

In addition, at least some of identified neoepitopes can also be used to generate one or more antibodies (e.g. monoclonal, polyclonal) against those neoepitopes. Then, the treated cells may further be exposed to antibodies against those neoepitopes. Among other benefits, it is contemplated that addition of such antibodies will be effective to increase ADCC in the tissue biopsy (and the patient).

While enhanced immunogenicity of tumor cells can be beneficial to enhance immune cell response, the immunogenicity should not significantly affect non-tumor cells. Thus, with respect to the best suitable treatment of the tumor cells to optimize immunogenicity it is contemplated that any treatment is suitable that is above control, and more typically at least 20%, or at least 40%, or at least 60% above control. Most preferably, such treatment is also less cytotoxic to non tumor cells in the tissue and the person of ordinary skill in the art will be readily able to determine optimal treatments that maximize immunogenicity and minimize cytotoxicity. For example, suitable outcomes for immunogenicity include lysis or apoptosis of the pretreated tumor cells and lack of lysis or apoptosis of non-tumor cells.

Once suitable treatments are identified, the patient may be treated using such agents and protocols to increase the likelihood of generating an acute (and preferably durable) immune response. Moreover, it should be appreciated that the treatment of the patient may be further augmented with immunotherapeutic virus compositions that will deliver recombinant nucleic acids that include genes encoding neoepitopes (and optionally other molecules, including co-stimulator molecules and check point inhibitors) as discussed above. To further increase an immune response, subsequent tumor biopsies may be taken to adjust or modify the therapeutic strategy to increase immunogenicity, following the basic principles as described herein. In this context, it should be appreciated that additional omics information may provide insights into (neo)epitopes that are critical for eliciting a therapeutically effective immune response. Indeed, the inventor contemplates that multiple such treatment identifications and treatments will lead to epitope spread or an antigen cascade that may advantageously 'cast a wider net' against tumor epitopes and neoepitopes. Lastly, it is contemplated that where checkpoint inhibitors are used, such inhibitors may be locally administered to the tumor to reduce potential issues with an uncontrolled (auto)immune response.

In some embodiments, the numbers expressing quantities or ranges, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified, thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The invention claimed is:

1. A method of identifying a treatment option for a cancer patient, the method comprising:
   obtaining a biopsy sample from a tumor of the cancer patient, dividing the biopsy sample into a plurality of biopsy samples, and ex vivo exposing each of the plurality of biopsy samples to distinct stress conditions to produce respective pretreated tumor cells, wherein the stress conditions are selected from the group consisting of a low-dose chemotherapy, exposure to a native or genetically modified T-cell, exposure to a native or genetically modified Natural Killer (NK) cell, exposure to an antibody, and an environmental stress condition;
   contacting each of the pretreated tumor cells with a plurality of immune competent cells;
   quantifying a response of the immune competent cells to each of the pretreated tumor cells; and
   selecting from the stress condition a treatment option when the response to the selected stress condition meets or exceeds a predetermined threshold rate of lysis or apoptosis of the pretreated tumor cells.

2. The method of claim 1, wherein the low-dose chemotherapy comprises a metronomic low-dose chemotherapy.

3. The method of claim 1, wherein the environmental stress condition is selected from the group consisting of a DNA damaging agent, a heat shock protein 90 (HSP90) inhibitor, a glycogen synthase kinase 3 (GSK3) inhibitor, and a virus infection.

4. The method of claim 1, wherein the pretreated tumor cells overexpress natural killer group 2, member D (NKG2D) ligand relative to the same cell without exposure to the stress condition.

5. The method of claim 1, further comprising a step of exposing at least one of the plurality of biopsy samples to an immune stimulant, wherein the immune stimulant is coadministered with the at least one stress condition.

6. The method of claim 5, wherein the immune stimulant is a cytokine.

7. The method of claim 6, wherein the cytokine is selected from the group consisting of IL-15, IL-15 superagonist, IL-2, IL-7, and IL-21.

8. The method of claim 5, wherein the immune stimulant is a Toll-like receptor (TLR) ligand.

9. The method of claim 5, wherein the immune stimulant is a checkpoint inhibitor.

10. The method of claim 1, further comprising a step of determining a plurality of neoepitopes for the biopsy sample.

11. The method of claim 10, further comprising a step of generating an antibody against at least one of the plurality of neoepitopes.

12. The method of claim 10, further comprising a step of generating a viral vector that contains a recombinant nucleic acid that encodes at least one of the plurality of neoepitopes, and contacting the immune competent cells with the viral vector.

13. The method of claim 10, further comprising a step of determining a second plurality of neoepitopes for the pretreated tumor cells.

14. The method of claim 1, wherein the step of quantifying the response of the immune competent cells comprises a microscopic assay, a luminescent assay, a fluorescent assay, or a radiological assay.

15. The method of claim 1, wherein the predetermined threshold is a predetermined rate of lysis or the rate of apoptosis of the pretreated tumor cells is less than 10% of all cells in the tissue.

* * * * *